United States Patent [19]
Fitch et al.

[11] Patent Number: 5,385,043
[45] Date of Patent: Jan. 31, 1995

[54] CONTAMINATION MEASUREMENT APPARATUS

[75] Inventors: James C. Fitch; Zhan Wu, both of Tulsa, Okla.

[73] Assignee: Diagnetics, Inc., Tulsa, Okla.

[21] Appl. No.: 137,609

[22] Filed: Oct. 15, 1993

[51] Int. Cl.⁶ ............................................. G01N 15/06
[52] U.S. Cl. .................. 73/61.73; 73/61.71; 110/179; 131/300
[58] Field of Search ............ 110/179; 73/61.71, 61.73; 131/300

[56] References Cited

U.S. PATENT DOCUMENTS

| | | | |
|---|---|---|---|
| 2,040,042 | 5/1936 | Eckstein | 73/61.73 |
| 3,050,987 | 8/1962 | Osgood | 73/61.73 |
| 3,357,236 | 12/1967 | Kasten | 73/61.73 |
| 3,455,146 | 7/1969 | Smith et al. | 73/61.73 |
| 3,686,925 | 8/1972 | Fleisch et al. | 73/61.73 |
| 3,837,216 | 9/1974 | Shinohara et al. | 73/61.73 |
| 4,468,954 | 9/1984 | Lanctot et al. | 73/61.73 |
| 4,663,966 | 5/1987 | Fisher et al. | 73/61.73 |
| 5,266,495 | 11/1993 | Lapidus | 73/61.73 |

Primary Examiner—Thomas P. Noland
Assistant Examiner—J. David Wiggins
Attorney, Agent, or Firm—Head & Johnson

[57] ABSTRACT

A contamination measurement apparatus for determining a level of particulate contamination in a fluid. The apparatus includes a filter for passing a fluid therethrough. A volume indicator produces movement of a test piston in response to the fluid passing through the filter. The flow decay characteristics of the fluid are determined in response to movement of the test piston. A back flush mechanism returns the fluid back through the filter by use of a back flush piston which reciprocates in a chamber between a first position wherein the back flush piston is engaged with the test piston, and a second position wherein the back flush piston is disengaged from the test piston so that the test piston is free to move in response to the fluid volume.

14 Claims, 3 Drawing Sheets

CONTAMINATION MEASUREMENT APPARATUS

BACKGROUND OF THE INVENTION

1. Field of the Invention

The present invention relates to an apparatus for dynamic fluid sampling. In particular, the present invention relates to an apparatus for determining the level of particulate contaminates in fluid within a fluid system.

2. Prior Art

In many fluid systems, such as hydraulic, lubricating, transmission, gear, fuel, and many process systems, it is essential to detect and measure the concentration of particulate contaminants which are entrained or suspended in the fluids. High levels of such contamination will dramatically decrease the efficiency and life of machinery associated with the fluids.

The analysis of fluids in a system can suggest maintenance procedures to improve equipment reliability and extend system life.

The condition of the fluid, therefore, is of preeminent concern and should be monitored regularly. In some systems, it is so important that daily monitoring is not frequent enough. The analysis should be done quickly in the field.

One known system for determining the level of contamination in a fluid is by passing portions of the system fluid through a filter until a predetermined pressure differential is achieved across the filter medium. The level of contamination in the fluid is determined by measuring the time required to reach the predetermined pressure level. Another known system determines the rate of change of the pressure differential across the filter medium. These systems are subject to the effects from system flow rate, system pressure differential, and fluid viscosity. Other measurement devices require achievement of a constant or known flow rate in the mechanism.

Some of these systems require personnel to mechanically back flush the fluid to take additional readings. Even automated systems suffer certain limitations. As one example, certain automated systems contain many fluid flow paths resulting in cross contamination or mixing between test cycles.

There exists a need to provide a contamination measurement apparatus that will continuously monitor the particulate contamination in fluid and that is not temperature or viscosity dependent.

It is, therefore, a principal object and purpose of the present invention to provide a contamination measurement apparatus that will continuously monitor the particulate level in the fluid system.

It is an additional object and purpose of the present invention to provide a contamination measurement apparatus that is insensitive to temperature variations of the fluid or the ambiance.

It is a further object and purpose of the present invention to provide a contamination measurement apparatus that is insensitive to the fluid viscosity.

It is a further object and purpose of the present invention to provide an unattended contamination measurement apparatus.

It is a further object and purpose of the present invention to provide a contamination measurement apparatus that will purge all fluid from the apparatus to avoid contamination between test cycles.

SUMMARY OF THE INVENTION

The present invention provides an contamination apparatus that may be connected inline to a fluid system. Fluid from the system would be directed through an inlet line and an inlet port. An outlet port from the apparatus leads to a system sink or a low pressure return line. A source of fluid from the fluid system to be monitored is, thus, supplied.

A removable screen plug provides access to an open end cap. When in place, the end cap provides fluid communication between the inlet port and the outlet port. The end cap and screen plug together form a passage leading to a test screen.

The test screen is a porous filter medium having pore dimensions, pore densities and screen area selected and defined for precise calibration. During a measurement test, fluid passes through the screen, leaving particles on the screen's surface. The particles gradually close off the available pores and flow through the screen is thereby reduced. After a test, trapped particles are released from the screen by a back flushing procedure.

On the opposite side of the test screen is a passageway leading to a cylindrical test chamber within a cylindrical body.

A test piston is allowed to move within the test chamber creating a fluid tight seal with the walls of the test chamber. Axially extending from the test piston is a piston rod which passes through a substantial portion of the apparatus. The test piston rod is linked to a displacement sensor which moves in response to movement of the piston rod. The displacement sensor acts as a gauge head for a stationary linear gauge.

A stop collar surrounds the piston rod but allows the piston rod to travel through an axial opening therein. The stop collar resides within a shoulder formed in the cylindrical body. A snap ring is rigidly affixed to the piston rod and radially extends therefrom. Movement of the piston rod, therefore, moves the snap ring.

A back flush cylinder extends from the cylinder body. A back flush piston reciprocates within the back flush cylinder body. The back flush piston and rod have a hollow axial core within which freely passes the test piston rod. The snap ring extending from the test piston rod provides a single direction engagement between the test piston rod and the back flush piston rod.

The testing procedure of the measurement apparatus may be divided into two strokes—the measuring stroke and the back flush stroke. Just prior to the measurement stroke, the test piston abuts and is flush against the end cap so that the test chamber is closed off. The back flush piston is pushed firmly up against the snap ring, forcing the test piston rod fully forward until its surface touches the end cap. Additionally, the displacement sensor is at a zero position. Air pressure is directed from a pressure source through an air pressure port causing the back flush piston to move in a direction away from the snap ring and away from the test piston. By retracting the back flush piston, the measurement stroke can be initiated.

As soon as the back flush piston is retracted, the snap ring loses contact with the back flush piston rod. Since no force is thereafter applied on the snap ring, the test piston rod will be allowed to move under hydraulic force of the test piston. The pressurized fluid in the system will pass through the test screen and cause the test piston to move. The speed or velocity of the moving test piston is calculated from displacement of the piston rod as measured by a linear gauge. This displacement is relayed to a data acquisition unit in order to determine and calculate the change of speed or velocity of the piston rod for the purpose of calculating the particle count of the fluid.

The test piston keeps moving in response to fluid moving through the screen until the snap ring comes into contact with the back flush piston rod again or until a signal is sent that an adequate reading from the linear gauge has been taken.

The back flush stroke is thereafter initiated. A valve is switched so that air under pressure is delivered through an alternative air pressure port into the cylindrical body. Under air pressure, the back flush piston rod will be driven in the opposite direction toward the snap ring and toward the test piston. The hollow back flush piston rod engages and pushes the snap ring which, in turn, drives the test rod and test piston back into the initial position against the end cap while, at the same time, reversing flow through the screen to clean the screen and purge particles from the apparatus. Thereafter, the apparatus is set to begin another test cycle.

DETAILED DESCRIPTION OF THE PREFERRED EMBODIMENT

Figure 1:
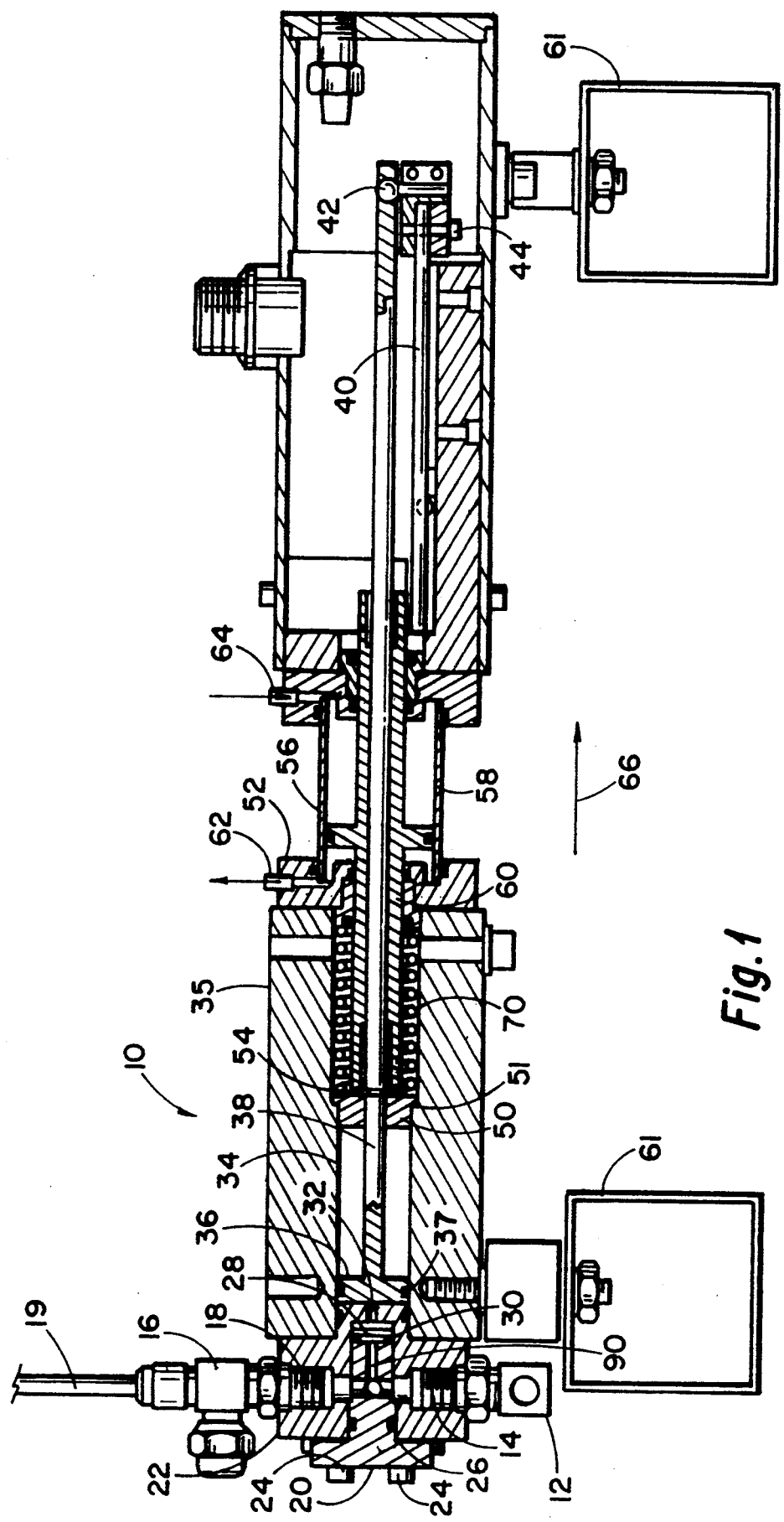
FIG. 1 is partial sectional view of an inline contamination measurement apparatus constructed in accordance with the present invention wherein the measuring stroke is set to be initiated.

Referring to the drawings in detail, FIG. 1 illustrates a partial cross sectional view of a contamination measurement apparatus constructed in accordance with the present invention. The apparatus 10 would be connected to a fluid system such as a hydraulic system. It will be understood that the present invention has numerous applications in various fluid systems.

Fluid from the system (not shown) would be directed into and through an inlet line (not shown) and an inlet port 12 which may have a threaded connection 14 with the apparatus.

An outlet port 16 having a threaded connection 18 with the apparatus 10 leads to a system sink or low pressure return line 19. A source of fluid from the fluid system to be monitored is, thus, supplied.

Depending on the particular system involved, a pressure regulator (not shown in FIG. 1) may be required to keep a somewhat constant pressure prior to introduction of the fluid at the inlet port of the apparatus. As an example, a fluid system having a pressure of approximately 2000 psi may have a pressure regulator to step down the pressure to 60 psi. The desirability of a regulated fluid pressure will be appreciated from the description to follow.

A removable screen plug 20 provides access to an open end cap 22. The screen plug 20 may be secured to the end cap 22 by screws 24 or other fasteners. When in place, the end cap provides fluid communication between the inlet port and the outlet port. The end cap 22 may include an O-ring or other gaskets 26 to insure a fluid tight seal.

The end cap and screen plug together form a passage 90 leading to a test screen 28. The test screen is, thus, readily accessible for maintenance or replacement. An O-ring or O-rings 30 assist in retaining the test screen 28 in place and prevent fluid flow around the test screen. As will be observed, mechanical filtration of particulate matter is used to determine solid contaminant levels in fluid. This is accomplished by use of the test screen 28.

The test screen 28 is a porous filter medium which is formed of any of several known materials. The filter screen may be a wire screen, an electro-formed metal screen, a sintered metal or a synthetic thermoplastic screen consisting of a thermal set plastic arranged on a woven monofilament fabric. The exact pore dimension and pore density and screen area are selected and defined for precise calibration. The screen may be ultrasonically fused between washers or held in press fit or other suitable housing of an exact internal diameter to prevent any change in calibration.

During a measurement test, fluid will pass through the screen leaving particles on the screen's surface. The particles gradually close off available pores and flow through the screen is thereby reduced. After a test, trapped particles are released from the test screen 28 by a back flushing procedure which will be described herein.

On the opposite side of the test screen is a passageway 32 leading to a cylindrical test chamber 34 within a cylindrical body 35.

A test piston 36 is allowed to move within the test chamber 34. The test piston may have gaskets 37 to maintain a fluid tight seal with the walls of the test chamber. Axially extending from the test piston is a piston rod 38 which is shown partially in section in FIG. 1. The test piston passes through a substantial portion of the apparatus 10 and is linked to a linear gauge 40 which moves in response to the piston rod. The piston rod is connected to the linear gauge through a pin 42 and a fastener or fasteners 44.

Linear movement of the test piston will, thus, move the linear gauge linearly.

Other analog or digital linear gauges could be used to track the position of the test piston rod.

A stop collar 50 surrounds the piston rod 38 but allows it to travel through an axial opening in the stop collar. The stop collar 50 resides within and abuts a shoulder 51 of the cylinder body 35.

An o-ring or snap ring 54 is rigidly affixed to the piston rod 38 and radially extends therefrom. Movement of the piston rod, therefore, moves the snap ring 54.

A back flush cylinder 56 extends from the cylinder body. A back flush piston 58 reciprocates within the back flush cylinder. The back flush piston 58 and a back flush rod 60 have a hollow axial core within which passes freely the test piston rod 38. The inner diameter of both the hollow back flush piston and the rod are larger than the diameter of the test piston rod. The snap ring 54 provides a single direction engagement between the test piston rod 38 and the back flush piston 58.

The apparatus 10 may be attached by fasteners to tubes 61 or otherwise secured.

The testing procedure for the measurement apparatus 10 may be divided into two strokes—the measuring stroke and the back flush stroke. FIG. 1 illustrates the measurement apparatus wherein the test piston 36 has closed off the test chamber 34 so that no fluid is allowed to pass therein. The apparatus is set to begin a measurement operation.

In FIG. 1, the apparatus is set to begin the measuring stroke. The back flush piston rod 60 is firmly up against the snap ring 54, forcing the test piston rod 38 to move fully forward until its surface touches the end cap 22. In this position, no fluid is allowed to flow through the test screen 28 and into the test chamber 34. Additionally, in this position the displacement sensor 40 is at a zero position.

To begin the measurement operation, air pressure is directed from a pressure source (not shown) through an air pressure port 62 in the back flush cylinder 56. At the same time, air pressure port 64 is allowed to exhaust. Since the back flush cylinder 56 is a sealed container, this will cause the back flush piston 58 to move in a direction shown by arrow 66 in FIG. 1. By retracting the back flush piston 58 in this manner, the measurement stroke can be initiated. The back flush piston will move under air pressure until it has moved the length of the cylinder 56.

As soon as the back flush piston 58 is retracted, the snap ring 54 loses contact with the back flush cylinder piston rod 60. Since no force is thereafter applied on the snap ring, the test piston rod 38 will be allowed to move under force on the test piston 36. The pressurized fluid in the system will then be allowed to pass through the test screen 28 and cause the test piston to move. The speed or velocity of the moving test piston 36 is sensed or picked up by the linear gauge 40 and relayed to a data acquisition unit (not shown in FIG. 1). It is known that the test piston rod will slow down as the particulate matter accumulates on the screen. The information on the change in speed of the test piston as the fluid moves is used to determine and calculate the particle count of the fluid. By monitoring the change in speed of the piston rod, the level of particulate matter is determined.

The test piston keeps moving in response to fluid moving through the screen until the snap ring comes into contact with the back flush piston rod again or until a signal is sent that an adequate reading from the linear gauge 40 has been taken. This signal is sent by software commands in the data acquisition unit. The measuring stroke is terminated at this point.

Figure 2:
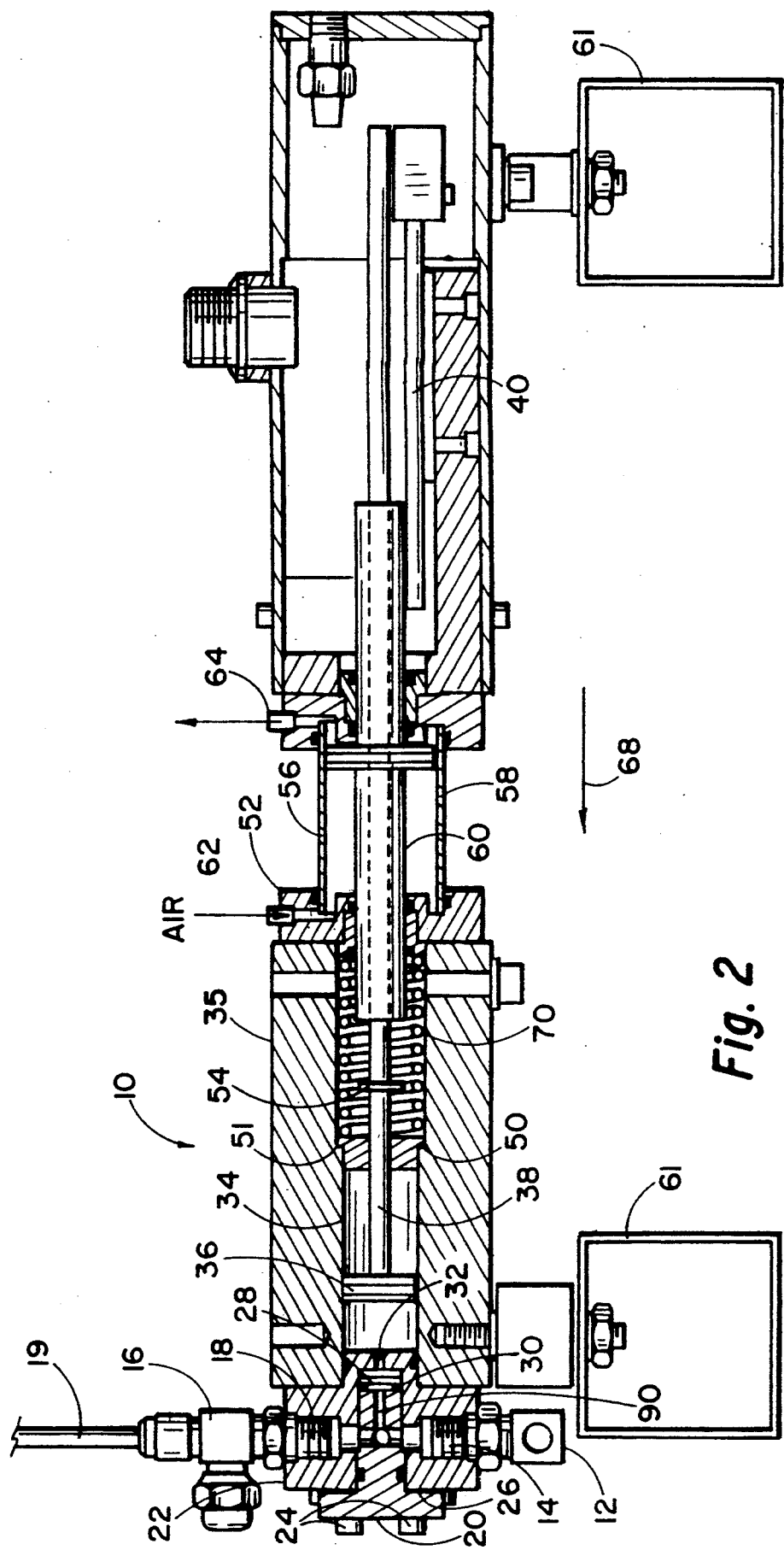
FIG. 2 is a partial sectional view of an inline contamination measurement apparatus as shown in FIG. 1 wherein the back flush stroke is set to be initiated.

The back flush stroke is thereafter initiated. FIG. 2 illustrates the apparatus 10 prior to initiation of the back flush stroke. A valve (not shown in FIGS. 1 or 2) is switched so that air under pressure is delivered through air pressure port 64 into cylinder 56. At the same time, air pressure port 62 is vented to atmosphere. Under air pressure, back flush piston 58 will be driven in the opposite direction as shown in arrow 68. The hollow back flush piston rod engages and pushes the snap ring 54 which, in turn, drives the test piston rod and the test piston back into the initial position against the end cap to begin another cycle and begin another test.

A spring 70 surrounding the back flush piston rod 60 engages stop collar 50 to retain it in position.

As the test piston 36 moves toward the end cap, the fluid in the test chamber 34 is forced back through the test screen, thereby back flushing contaminants on the screen to clean the screen and purge the contaminants from the device.

A salient feature of the present invention is the ability to purge the accumulated contaminants from the device to avoid mixing of test cycles. It is known that during the back flush stroke, the accumulated contaminants will move off of the screen during the initial stages. The volume of the test chamber 34 is significantly larger than the volume of the passageway 90 leading up to the filter so that the back flush stroke will completely flush away all contaminants accumulated on the screen.

In addition, the air pressure in the cylinder 56 has been arranged so that the back flush fluid pressure exceeds the test pressure of the fluid.

Figure 3:
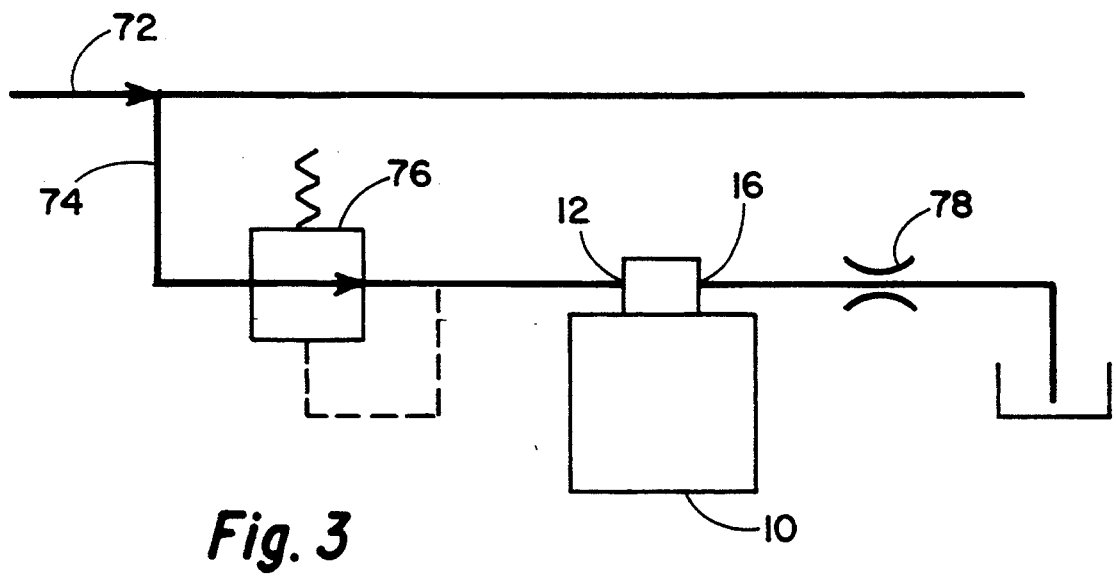
FIG. 3 is a simplified schematic diagram of the air pressure system for the back flush mechanism of the apparatus.

FIG. 3 illustrates a simplified diagram of the fluid system 72 as it interfaces with the apparatus. Fluid from the system would be led through a lead line 74 to a pressure regulator 76 to provide an even pressure to fluid entering the apparatus 10. Fluid from the outlet would pass through a restriction 78 to maintain the pressure.

Figure 4:
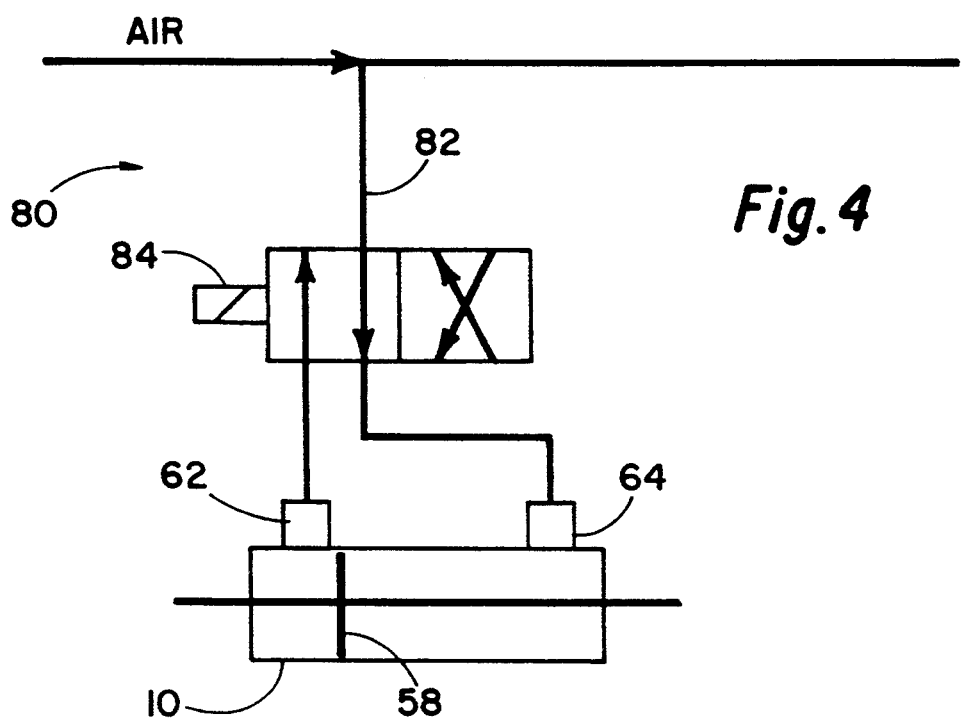
FIG. 4 is a simplified schematic diagram of the fluid system in which the apparatus is utilized.

FIG. 4 illustrates a simplified diagram of an air pressure system 80 to pressurize the cylinder 56. Air under pressure is passed through a solenoid activated valve 84. The valve may be switched to pressurize opposite sides of the back flush piston.

It will be seen that with the use of the present apparatus, the back flush stroke and back flush operation are isolated from the test system during the test stroke, therefore the displacement signal is not interfered with by the back flush device. Only after the measurement stroke is finished is the back flush cylinder engaged into the system by pushing against the snap ring mounted on the test piston rod. The present invention will allow unattended, automatic monitoring and allow automatic checking of the system status thereby enabling proactive maintenance decisions through continuous monitoring of the fluid system.

Whereas, the present invention has been described in relation to the drawings attached hereto, it should be understood that other and further modifications, apart from those shown or suggested herein, may be made within the spirit and scope of this invention.

What is claimed is:

1. A contamination measurement apparatus for determining a level of particulate contamination in a fluid, which apparatus comprises:
   a filter and means for passing a fluid through the filter;
   means to determine flow decay characteristics of said fluid in response to the volume of said fluid passing through said filter; and
   a back flush piston arranged to return said fluid back through said filter, said back flush piston being, in a first mode, engagable with said means to determine flow decay characteristics and, in a second mode, disengagable from said means to determine flow decay characteristics.

2. A contamination measurement apparatus as set forth in claim 1 wherein said means to determine flow decay characteristics includes a test piston coupled to a linear gauge.

3. A contamination measurement apparatus as set forth in claim 1 wherein said back flush means includes axial actuator means to move a back flush piston to urge said fluid back through said filter means.

4. A contamination measurement apparatus for determining a level of particulate contamination in a fluid, which apparatus comprises:
   a filter and means for passing a fluid through a filter;

volume indicator means for producing movement of a test piston in response to passing said fluid through said filter means;

means to determine flow decay characteristics of said fluid in response to said movement of said test piston; and back flush means to return said fluid back through said filter means, said back flush means having a back flush piston reciprocating in a chamber between a first position wherein said back flush piston is engaged with said test piston and said test piston is urged to prevent movement of said test piston and a second position wherein said back flush piston is disengaged from said test piston so that said test piston is free to move in response to said fluid.

5. A contamination measurement apparatus as set forth in claim 4 wherein said chamber of said back flush means includes air pressure means connected on both sides of said reciprocating back flush piston to pressurize said chamber.

6. A contamination measurement apparatus as set forth in claim 5 including a solenoid-operated switch to alternatively pressurize said sides of said reciprocating back flush piston.

7. A contamination measurement apparatus as set forth in claim 5 wherein said air pressure means on one said side of said back flush piston moves said test piston to said first position.

8. A contamination measurement apparatus as set forth in claim 5 wherein said air pressure means on said opposite side of said back flush piston moves said test piston to said second position.

9. A contamination measurement apparatus as set forth in claim 4 including means to activate said back flush means in response to said determination of flow decay characteristics.

10. A contamination measurement apparatus as set forth in claim 4 wherein said flow decay characteristics of said fluid are determined by change in the speed of movement of said test piston.

11. A contamination measurement apparatus as set forth in claim 4 including a test piston rod extending axially from said test piston and wherein said test piston and said back flush piston are axially aligned with said test piston rod passing through said back flush piston.

12. A method of determining a level of particulate contamination in a fluid system, which method comprises:

passing a portion of said fluid in a first direction through a filter;

producing movement of a test piston in response to said passing of said fluid through said filter;

determining flow decay characteristics in response to movement of said test piston; and engaging said test piston with a back flush piston rod to displace said test piston to pass said fluid back through said filter; and disengaging said back flush piston from said test piston.

13. A method of determining a level of particulate contamination as set forth in claim 12 wherein said back flush piston travels in a sealed chamber and is reciprocated by air pressure means.

14. A method of determining a level of particulate contamination as set forth in claim 13 wherein said flow decay characteristics are determined by monitoring change in the speed of movement of said test piston.

* * * * *